US006709404B1

(12) United States Patent
Creedon et al.

(10) Patent No.: US 6,709,404 B1
(45) Date of Patent: Mar. 23, 2004

(54) PHARYNGOMETER WITH DETACHABLE WAVETUBE

(75) Inventors: Dennis Creedon, Sandwich, ME (US); Philip Drinker, Belmont, MA (US); Gary Glass, Cambridge, MA (US); Lewis H. Marten, Westwood, MA (US); Anthony Sacchetti, Weymouth, MA (US)

(73) Assignee: E Benson Hood Laboratories, Pembroke, MA (US)

( * ) Notice: Subject to any disclaimer, the term of this patent is extended or adjusted under 35 U.S.C. 154(b) by 0 days.

(21) Appl. No.: 09/626,607

(22) Filed: Jul. 27, 2000

(51) Int. Cl.[7] .................................................. A61B 5/00
(52) U.S. Cl. ...................................... 600/538; 600/529
(58) Field of Search .................................. 600/529–538

(56) References Cited

U.S. PATENT DOCUMENTS

| | | | | |
|---|---|---|---|---|
| 5,047,044 A | * | 9/1991 | Smith et al. ................ 606/182 |
| 5,373,851 A | * | 12/1994 | Reinhold, Jr. ............... 600/538 |
| 5,848,973 A | | 12/1998 | Lane | |
| 5,882,314 A | | 3/1999 | Fredberg et al. | |
| 6,017,315 A | * | 1/2000 | Starr et al. .................. 600/538 |
| 6,148,815 A | * | 11/2000 | Wolf ....................... 128/205.23 |
| 6,176,833 B1 | * | 1/2001 | Thomson .................... 600/538 |
| 6,183,423 B1 | * | 2/2001 | Gaumond et al. ...... 600/538 X |
| 6,196,223 B1 | * | 3/2001 | Belfer et al. ........... 128/206.25 |

FOREIGN PATENT DOCUMENTS

| | | |
|---|---|---|
| WO | WO 93/11703 | 6/1993 |
| WO | WO 94/09700 | 5/1994 |

* cited by examiner

*Primary Examiner*—Robert L. Nasser
(74) *Attorney, Agent, or Firm*—Frommer Lawrence & Haug LLP; Ronald R. Santucci

(57) ABSTRACT

A pharyngometer or similar wavetube-based apparatus which includes a wavetube which is detachable from the electronic platform. As the wavetube includes no electronic components, the wavetube can be sterilized thermally or chemically between patients without damaging the electronics of the electronic platform. The wavetube is attached to the electronic platform by a tab in the electronic platform which fits into a lateral groove within the wavetube. Similarly, a threaded member in the electronic platform engages a threaded aperture in the wavetube.

7 Claims, 6 Drawing Sheets

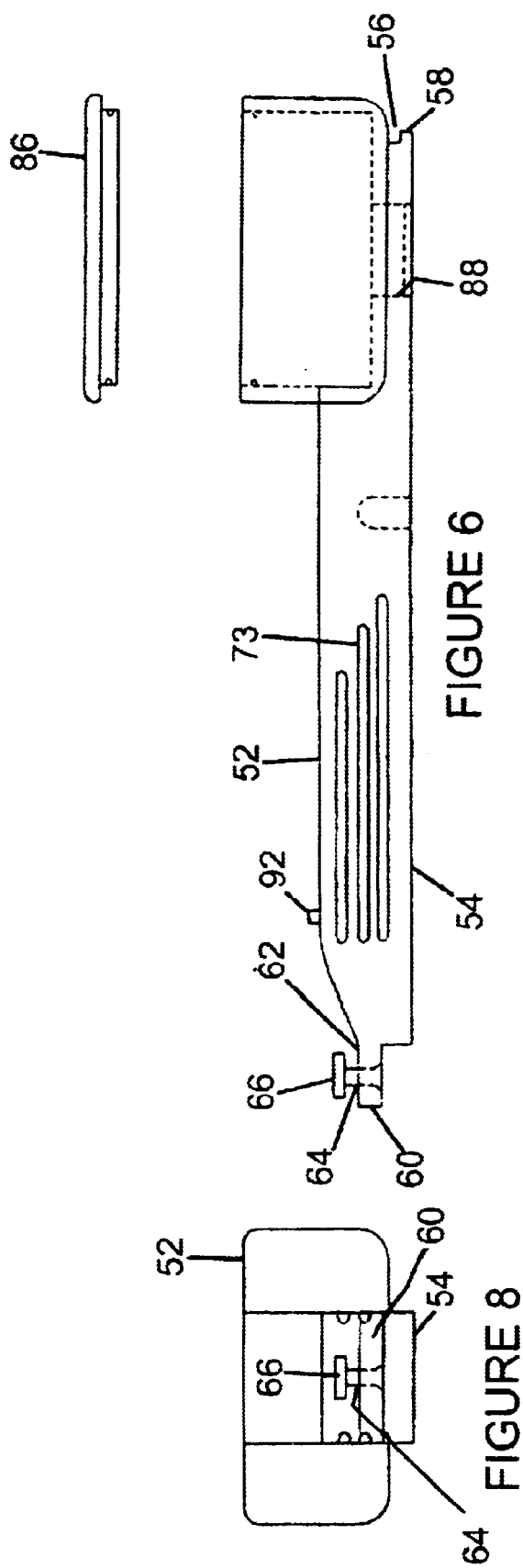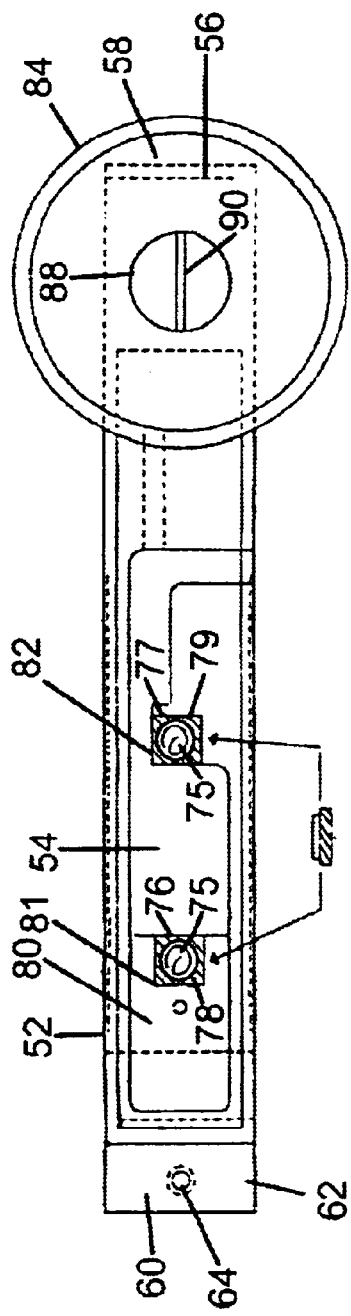

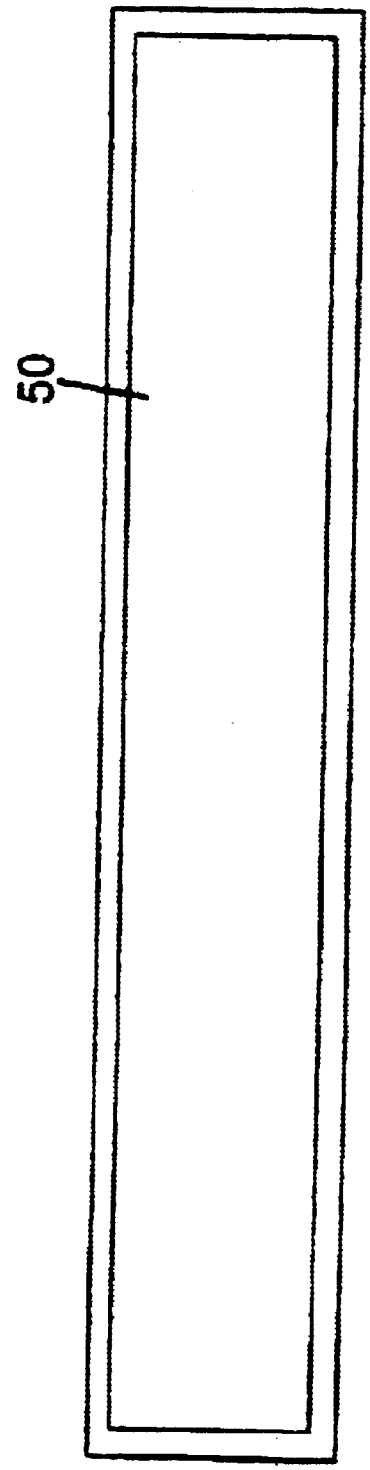
FIGURE 10
FIGURE 9

PHARYNGOMETER WITH DETACHABLE WAVETUBE

BACKGROUND OF THE INVENTION

1. Field of the Invention

This invention pertains to a pharyngometer, or other wavetube-based device, in which the wavetube can be detached from the electronic platform.

2. Description of the Prior Art

In the prior art, pharyngometers are known. However, these devices have typically included electronics which were affixed to the wavetube. This was disadvantageous in that it was difficult to sterilize the wavetube after use by a patient with the electronics attached. However, such sterilization is necessary to prevent cross-contamination between patients.

OBJECTS AND SUMMARY OF THE INVENTION

It is therefore an object of the invention to provide a pharyngometer, or other wavetube-based device, in which the wavetube can be easily sterilized.

This and other objects are attained by providing a pharyngometer, or similar wavetube-based device, wherein the wavetube can be detached from the electronics for cleaning and sterilization. The detached wavetube can be sterilized with heat or disinfectant, without damaging the electronics.

BRIEF DESCRIPTION OF THE DRAWINGS

Further objects and advantages of the invention will become apparent from the following description and claims and from the accompanying drawings, wherein:

FIG. 6 is a partially exploded side plan view of the electronic platform of the pharyngometer of the present invention.

FIG. 7 is a bottom plan view of the electronic platform of the pharyngometer of the present invention.

FIG. 8 is an end plan view of the electronic platform of the pharyngometer of the present invention.

FIG. 9 is a top plan view of the filter of the pharyngometer of the present invention.

FIG. 10 is a side plan view of the filter of the pharyngometer of the present invention.

DETAILED DESCRIPTION OF THE PREFERRED EMBODIMENT

Figure 1:
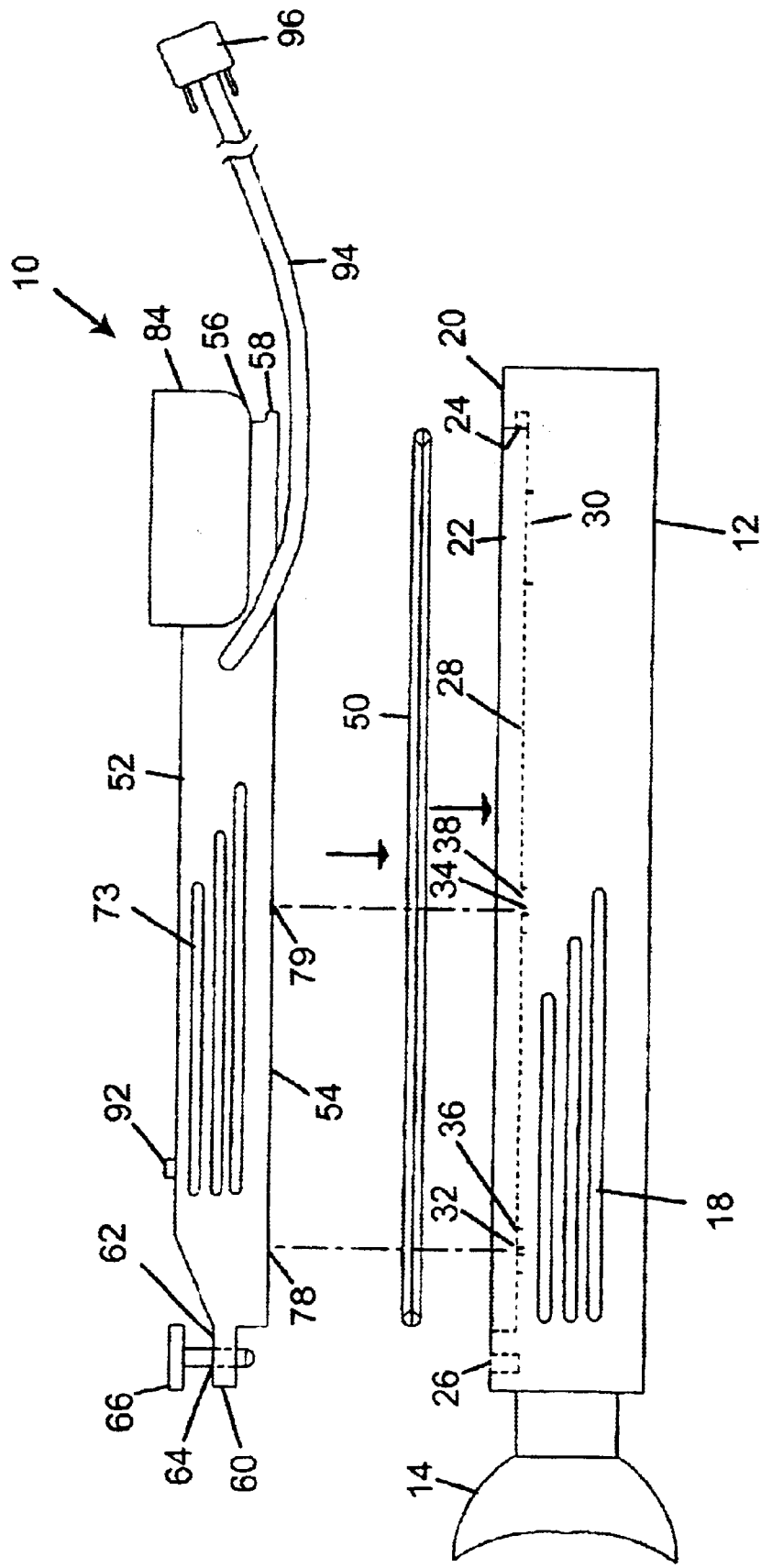
FIG. 1 is an exploded view of the pharyngometer of the present invention.

Referring now to the drawings in detail wherein like numerals refer to like elements throughout the several views, one sees that FIG. 1 is an exploded plan view of pharyngometer 10 of the present invention. The present invention can likewise be applied to other wavetube-based devices such as those directed to nasal tubes or tonsils. A description of the electronics and other operational features of the pharyngometer 10 can be found in U.S. Pat. No. 5,848,973 entitled "Filter for Use in an Acoustic Imaging Device", issued on Dec. 15, 1998 to Lane; PCT/US92/09236 filed on Oct. 27, 1992; PCT/US93/05819 filed on Jun. 16, 1993; U.S. Pat. No. 5,882,314 entitled "Airway Geometry Imaging" issued on Mar. 16, 1999 to Fredberg et al.; and U.S. patent application Ser. No. 08/283,074 filed on Jul. 29, 1994, the disclosures of which are hereby incorporated by reference.

Figure 3:
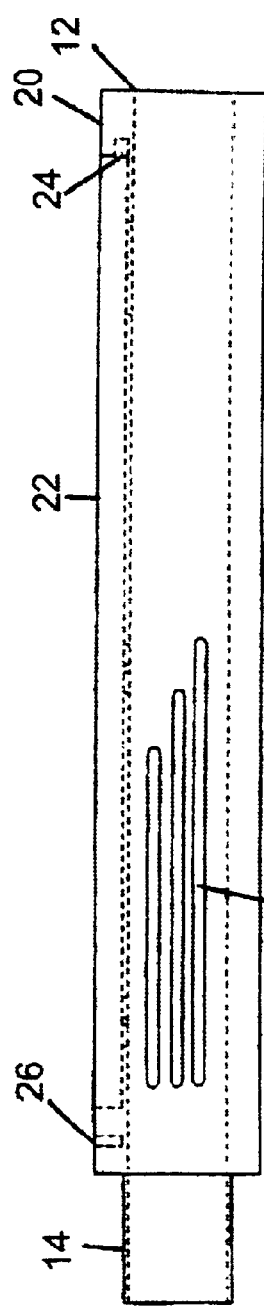
FIG. 3 is a side plan view of the wavetube of the pharyngometer of the present invention.
Figure 4:
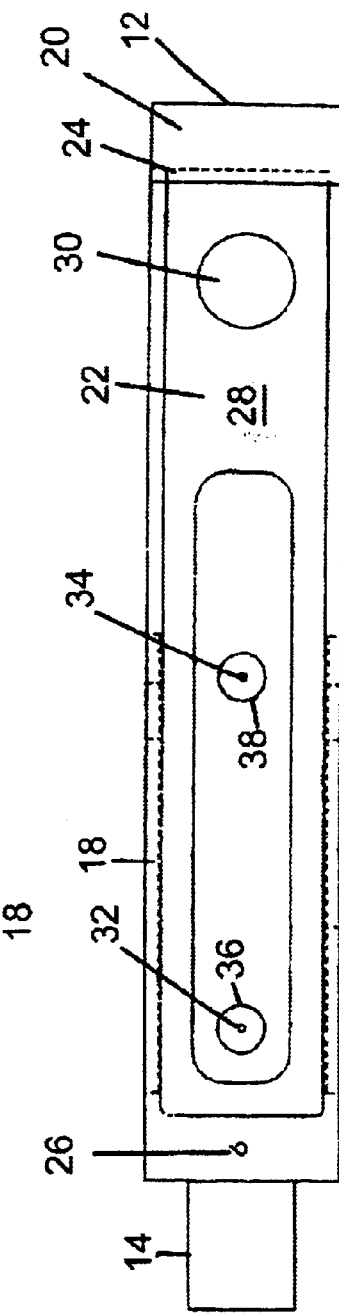
FIG. 4 is a bottom plan view of the wavetube of the pharyngometer of the present invention.
Figure 5:
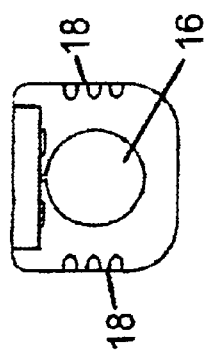
FIG. 5 is an end plan view of the wavetube of the pharyngometer of the present invention.

Wavetube 12 (also see FIGS. 3, 4 and 5) includes mouthpiece 14 provides communication to passageway 16. Wavetube 12 is generally rectangular and includes ribs 18 on the lateral sides thereof to assist in the gripping of wavetube 12 by a user. Upper surface 20 of wavetube 12 includes pocket 22 with lateral groove 24 on a first end thereof. Additionally, threaded aperture 26 is formed immediately outwardly adjacent from a second end of pocket 22. Floor 28 of pocket 22 further includes large aperture 30 leading to passageway 16. Similarly, small apertures 32, 34 are formed on raised circular locating disks 36, 38 on pocket 22.

Rectangular filter 50 (see FIGS. 9 and 10) is sized to fit into pocket 22. Rectangular filter 50 is typically multilayered polypropylene material, although those skilled in the art will recognize that there are equivalent materials. Filter 50 is heat sealed around the edge in order to create a frame-type structure which provides rigidity to filter 50 and which further aids in the insertion and positioning of filter 50 into the wavetube filter cavity. Filter 50 additionally creates an acoustic seal where the microphones 78, 79 sit on the wavetube 12.

Figure 2:
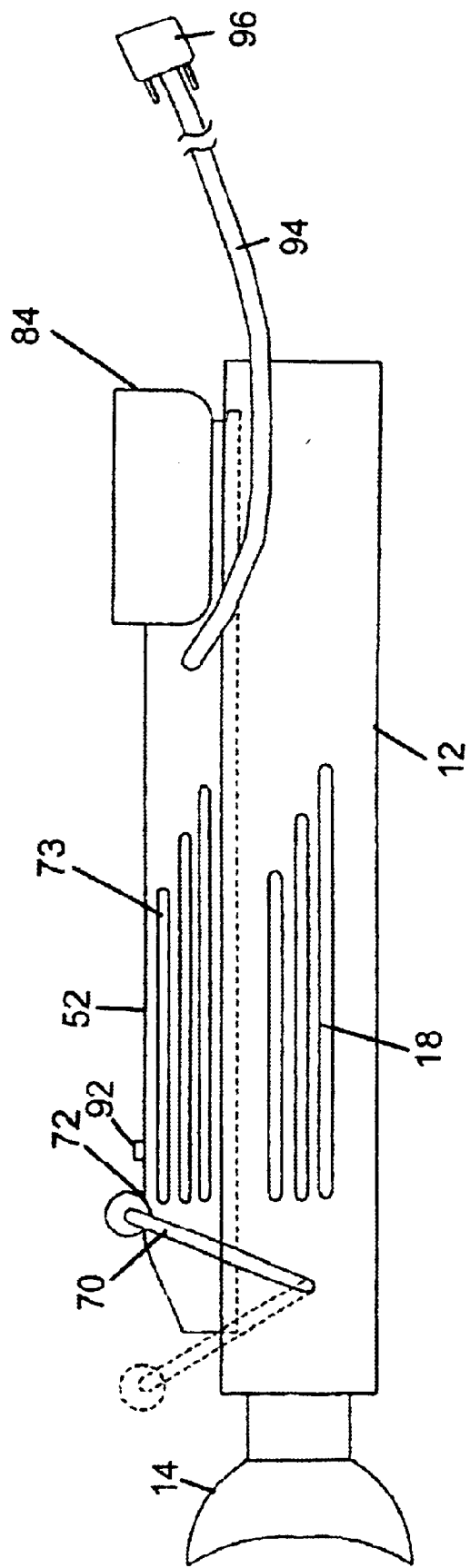
FIG. 2 is a plan view of an alternative embodiment of the pharyngometer of the present invention.

Electronic platform 52 includes lower planar surface 54 which is sized to fit into pocket 22 and impinge against rectangular filter 50. First end 56 of electronic platform 52 includes tab 58 formed on lower planar surface 54 which extends into lateral groove 24 of pocket 22. Second end 60 of electronic platform 52 includes vertically offset tab 62 with aperture 64 therethrough. Threaded member 66 passes through aperture 64 and is secured within threaded aperture 26 in order to secure tab 58 into lateral groove 24 thereby locking electronic platform 52 to wavetube 12. FIG. 2 shows an alternative embodiment wherein roller bar 70 swivels on wavetube 12 and engages detent groove 72 on the surface of electronic platform 52 in a locked position thereby replacing the threaded member 66 and associated structure of FIG. 1.

As shown in FIGS. 1, 2 and 6, grooves 73 are formed on the sides of electronic platform 52 to aid the user to grip pharyngometer 10.

Figure 12:
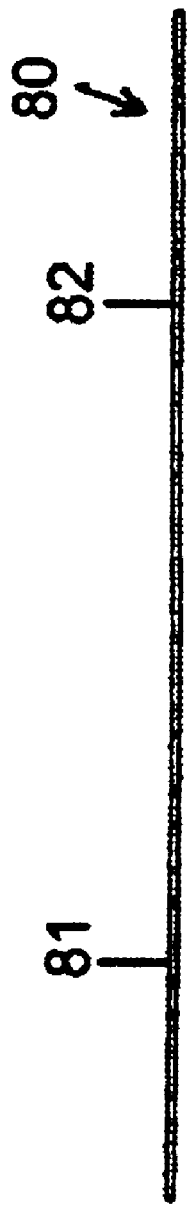
FIG. 12 is a side plan view of the cover plate of the pharyngometer of the present invention.
Figure 11:
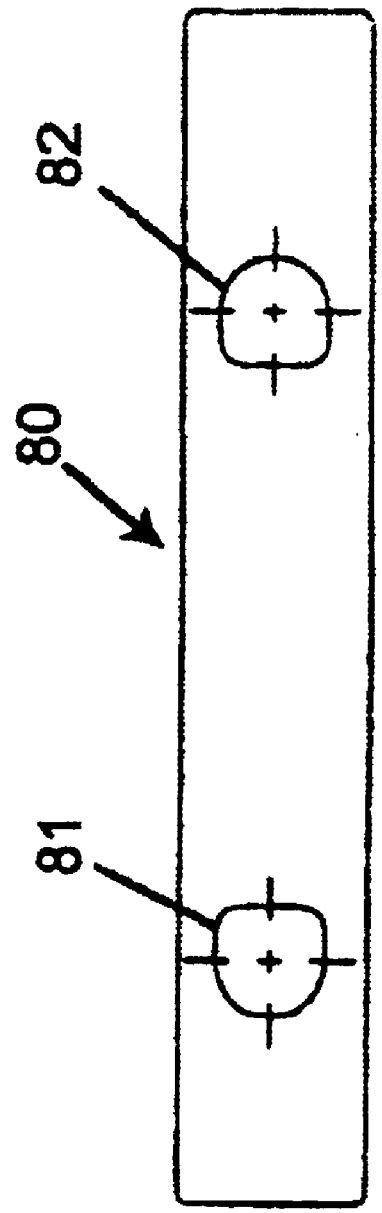
FIG. 11 is a top plan view of the cover plate of the pharyngometer of the present invention.

As shown in FIG. 7, the bottom surface 74 of electronic platform 52 includes apertures 76, 77 through which microphones 78, 79 extend. Microphones 78, 79 of FIG. 7 align with apertures 32, 34 of FIG. 4. Microphones 78, 79 are located on respective springs 75 made of silicone rubber or metal located internally in electronic platform 52 so as to provide the critical alignment and positioning of microphones 78, 79 over apertures 32, 34 on locating disks 36, 38 of wavetube 12 and apply the appropriate pressure thereto. Moreover, microphones 78, 79 are snugly held in place and precisely positioned by cover plate 80 (see FIGS. 7, 11 and 12) which has corresponding apertures 81, 82.

Cylindrical cavity housing 84 is formed on first end 56 of electronic platform 52 and includes a speaker (not shown).

Cylindrical cavity housing 84 includes a removable cap 86 (see FIG. 6) which snaps into place to hold the microphone in place. Furthermore, opening 88 extends from the interior of cylindrical cavity housing 84 communicating to large aperture 30. Bar 90 extends across opening 88 to shield the speaker from mechanical intrusion.

Button 92 on the upper surface of electronic platform 52 activates the computer software, microphones 78, 79 and the speaker in accordance with the prior references incorporated by reference.

Serial cable 94 provides power and information communication to pharyngometer 10 via serial connector 96 which, in turn, is connected to a personal computer or similar equipment (not shown).

With the present design, a user can detach wavetube 12 from electronic platform 52 by simply turning threaded member 66 and sliding tab 58 out of lateral groove 24. Wavetube 12 can then be sterilized by heat, liquid or other methods without damaging electronic platform 52.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A wavetube-based apparatus including:
    a wavetube portion which includes a passageway through which a user can expel air, said wavetube portion being free of electronic elements;
    an electronic platform with microphones impinging against said wavetube portion;
    wherein said wavetube portion and said electronic platform are separate elements; and
    means for attaching and detaching said wavetube portion from said electronic platform, wherein said microphones are located on a biasing means and positioned over apertures in said wavetube portion leading to said passageway when said wavetube is attached to said electronic platform.

2. The wavetube-based apparatus of claim 1 wherein said means for attaching and detaching includes a tab on a first of said wavetube portion and said electronic platform and a groove on a second of said wavetube portion and said electronic platform, wherein said tab fits into said groove.

3. The wavetube-based apparatus of claim 1 further including a filter between said wavetube portion and said electronic platform, said filter being sealed around edges thereof in order to impart rigidity to said filter.

4. The wavetube-based apparatus of claim 1 wherein the wavetube-based apparatus is a pharyngometer.

5. A wavetube-based apparatus including:
    a wavetube portion which includes a passageway through which a user can expel air, said wavetube portion being free of electronic elements;
    an electronic platform with microphones impinging against said wavetube portion;
    wherein said wavetube portion and said electronic platform are separate elements; and
    means for attaching and detaching said wavetube portion from said electronic platform, wherein said microphones are positioned over apertures in said wavetube portion leading to said passageway when said wavetube is attached to said electronic platform,
    wherein said means for attaching and detaching includes a tab on a first of said wavetube portion and said electronic platform and a groove on a second of said wavetube portion and said electronic platform, wherein said tab fits into said groove, and
    wherein said means for attaching and detaching further includes a threaded element which fits into a threaded aperture.

6. The wavetube-based apparatus of claim 5 further including a filter between said wavetube portion and said electronic platform.

7. A wavetube-based apparatus including:
    a wavetube portion which includes a passageway through which a user can expel air, said wavetube portion being free of electronic elements;
    an electronic platform with microphones impinging against said wavetube portion;
    wherein said wavetube portion and said electronic platform are separate elements; and
    means for attaching and detaching said wavetube portion from said electronic platform, wherein said microphones are positioned over apertures in said wavetube portion leading to said passageway when said wavetube is attached to said electronic platform,
    wherein said means for attaching and detaching includes a swiveling bar on a first of said wavetube portion and said electronic platform and a groove on a second of said wavetube portion and said electronic platform, wherein said swiveling bar fits into said groove in an attached position.

* * * * *